United States Patent
Wisdom et al.

(10) Patent No.: US 10,791,697 B2
(45) Date of Patent: Oct. 6, 2020

(54) RICE CULTIVAR RU1401105

(71) Applicant: THE BOARD OF TRUSTEES OF THE UNIVERSITY OF ARKANSAS, Little Rock, AR (US)

(72) Inventors: Debra Ahrent Wisdom, Stuttgart, AR (US); Karen A. K. Moldenhauer, Stuttgart, AR (US); Xueyan Sha, Stuttgart, AR (US); James Gibbons, Stuttgart, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/251,902

(22) Filed: Jan. 18, 2019

(65) Prior Publication Data
US 2020/0229372 A1  Jul. 23, 2020

(51) Int. Cl.
*A01H 5/10* (2018.01)
*A01H 6/46* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS

| | | |
|---|---|---|
| 6,281,416 B1 | 8/2001 | Moldenhauer |
| 8,134,058 B2 | 3/2012 | Moldenhauer |
| 8,431,805 B2 | 4/2013 | Moldenhauer |
| 8,440,892 B2 * | 5/2013 | Moldenhauer ........... A01H 5/10 435/410 |
| 9,398,750 B2 | 7/2016 | Moldenhauer |

OTHER PUBLICATIONS

PI 597046. 1994. Donated by R. Zeigler of Irri. U.S. National Plant Germ plasm System. Access date Nov. 2017. Available at www.npgsweb.ars-grin.gov.
Sha, X. Y., et al. "Registration of 'Jazzman'aromatic long-grain rice." Journal of plant registrations 5.3 (2011) 304-308.
Webb, B. D., et al. "Utilization characteristics and qualities of United States rice." Rice grain quality and marketing. IRRI, Manila, Philippines (1985) 25-35.
PVP Application No. 201200104 (Mermentau), app date: Jan. 20, 2012.
PVP Application No. 200900298 (Jazzman), app date: May 6, 2009.
PVP Application No. 201100296 (Jazzman-2), app date: Feb. 24, 2011.
PVP Application No. 201200129 (Della-2), app date: Feb. 17, 2012.
PVP Application No. 201300087 (Antonio), app date: Dec. 10, 2012.
PVP Application No. 201000279 (CL 181-AR), app date: Apr. 8, 2010.

* cited by examiner

*Primary Examiner* — Medina A Ibrahim
(74) *Attorney, Agent, or Firm* — Quarles & Brady LLP

(57) ABSTRACT

A rice cultivar designated RU1401105 is disclosed. The invention relates to the seeds of rice cultivar RU1401105, to the plants of rice cultivar RU1401105, to plant parts office cultivar RU1401105, and to methods for producing a rice plant produced by crossing rice cultivar RU1401105 with itself or with another rice variety. This invention also relates to rice cultivars, or breeding cultivars, and plant parts derived from rice cultivar RU1401105, to methods for producing other rice cultivars, lines or plant parts derived from rice cultivar RU1401105, and to the rice plants, varieties, and their parts derived from use of those methods. The invention farther relates to hybrid rice seeds, plants, and plant parts produced by crossing rice cultivar RU1401105 with another rice cultivar.

22 Claims, No Drawings

RICE CULTIVAR RU1401105

BACKGROUND OF THE INVENTION

The present invention relates to a new and distinctive rice cultivar, designated RU1401105.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 cm to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Long-grain cultivars have been traditionally grown in the southern states and generally receive higher market prices.

Rice, *Oryza sativa* L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel rice cultivar designated RU1401105. This invention thus relates to the seeds of rice cultivar RU1401105, to the plants of rice RU1401105, and to methods for producing a rice plant produced by crossing rice RU1401105 with itself or another rice line.

Thus, any such methods using rice variety RU1401105 are part of this invention: selfing, backcrosses, hybrid production, crosses to populations, and the like. All plants produced using rice variety RU1401105 as a parent are within the scope of this invention. Advantageously, the rice variety could be used in crosses with other, different, rice plants to produce first generation (F1) rice hybrid seeds and plants with superior characteristics.

In another aspect, the present invention provides for single gene converted plants of RU1401105. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant RU1401105. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, leaves, anthers, pistils, root tips, flowers, seeds, panicles, or stems. Still further, the present invention provides rice plants regenerated from the tissue cultures of the invention.

In addition to the exemplary aspects and embodiments described above, further aspects and embodiments will become apparent by study of the following description and examples.

Definitions

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Alkali Spreading Value. Indicator of gelatinization temperature and an index that measures the extent of disintegration of milled rice kernel in contact with dilute alkali solution. Standard long grains have 3 to 5 Alkali Spreading Value (intermediate gelatinization temperature).

Allele. Allele is any of one or more alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Apparent Amylose content. Amylose content is one of the most important grain characteristics to describe cooking behavior in each grain class, or type including long, medium or short grain. The apparent amylose content is provided as g/kg herein and refers to the amount of starch in the endosperm of milled rice that is amylose. Amylose values will vary depending on the growth environment of the rice.

Backcrossing. Backcrossing is a process in which a breeder repeatedly crosses hybrid progeny back to one of the parents, for example, a first generation hybrid F1 with one of the parental genotypes of the F1 hybrid.

Breeding. The genetic manipulation of living organisms.

Cell. Cell as used herein includes a plant cell, whether isolated, in tissue culture or incorporated in a plant or plant part.

Days to 50% heading. Average number of days from emergence to the day when 50% of all panicles are exerted at least partially through the leaf sheath. A measure of maturity.

Embryo. The embryo is the small plant contained within a mature seed.

Essentially all of the physiological and morphological characteristics. A plant having essentially all the physiological and morphological characteristics means a plant having the physiological and morphological characteristics of the cultivar, except for the characteristics derived from the converted gene.

F #. The "F" symbol denotes the filial generation, and the # is the generation number, such as F1, F2, F3, etc.

Gene. As used herein, "gene" refers to a unit of inheritance corresponding to DNA or RNA that code for a type of protein or for an RNA chain that has a function in the organism.

Genotype. Refers to the genetic constitution of a cell or organism.

Kernal Length (L). Length of a rice grain is measured as millimeters.

Kernal Width (W). Width of a rice grain is measured as millimeters.

Grain Yield. Grain yield is measured in pounds per acre and at 12.0% moisture. Grain yield of rice is determined by the number of panicles per unit area, the number of fertile florets per panicle, and grain weight per floret.

Haploid. A cell or organism having one set of the two sets of chromosomes in a diploid.

Harvest Moisture. The percent of moisture of the grain when harvested.

Head rice. Kernels of milled rice with greater than ¾ of a kernel unbroken.

Length/Width (L/W) Ratio. This ratio is determined by dividing the average length (L) by the average width (W).

Lodging Resistance (also called Straw Strength). Lodging is measured as a subjective rating and is percentage of the plant stems leaning or fallen completely to the ground before harvest. Visual scoring where 0%=all plants standing to 100%=all plant in plot are laying flat on the soil surface. Lodged plants are difficult to harvest and reduce yield and grain quality.

Milling yield. Milling yield is the total amount of milled rice (whole and broken kernels) recovered after removal of hulls, bran, and germ by milling and head-rice yield, the total amount of whole kernels recovered after milling. Values are expressed as weight percentage of the original paddy or rough rice sample that was milled. For example, a milling yield of 65/70 is a sample of 100 grams of rough rice that produced 65 grams of head rice and 70 grams of total milled rice.

Pedigree. Refers to the lineage or genealogical descent of a plant.

Plant. As used herein, the term "plant" includes reference to an immature or mature whole plant, including a plant from which seed, grain, or anthers have been removed. Seed or embryo that will produce the plant is also considered to be the plant.

Plant Height. Plant height in centimeters is taken from soil surface to the tip of the extended panicle at harvest.

Plant parts. As used herein, the term "plant parts" (or a rice plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an F1 rice plant produced from the cross of two rice plants where at least one plant includes rice cultivar LaKast and progeny further includes, but is not limited to, subsequent F2, F3, F4, F5, F6, F7, F8, F9, and F10 generational crosses with the recurrent parental line.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

DETAILED DESCRIPTION OF THE INVENTION

Rice cultivar RU1401105 originated from the cross of Jazzman/PI 597046, number 20090392 made in Stuttgart, Ark., in 2009 using a combination of hybridization, modified pedigree, and bulk breeding methods. Jazzman is a high yielding, conventional height, Jasmine-type aromatic, long grain rice with very good milling and excellent grain quality developed at Crowley, La. and described by Sha et al. (*J Plant Regist.*, 5:304-308 (2011)). PI 597046 is a plant introduction donated in 1994 by R. Zeiger of IRRI. The experimental designation for early evaluation of RU1401105 was STG12L-30-145, starting with a bulk of F5 seed from the 2012 panicle row L-30-145. RU1401105 was tested in the Arkansas Rice Performance Trials (ARPT) and the Cooperative Uniform Regional Rice Nursery (URRN) from 2014 to 2017 as entry RU1401105.

Rice cultivar RU1401105 (*Oryza sativa* L.), is a high yielding Jasmine-type aromatic, mid-season, long-grain rice cultivar with a similar maturity to rice cultivar 'Wells', and three days earlier than Roy J. Plants of RU1401105 have erect culms, green erect leaves, and glaborus lemma, palea, and leaf blades. The lemma and palea are straw colored with red apiculi, many of which fade to straw at maturity.

Kernels of RU1401105 are similar in weight and size to Wells. Individual milled kernel weights (in g ms/1,000 seeds) of RU1401105, RU1501102, Mermentau, RU1401105, Taggart, and Wells averaged 21.7, 23.3, 20.0, 20.7, 22.7, and 21.9, respectively, in the Arkansas Rice Performance Trials (ARPT) from 2014 to 2016.

Rice cultivar RU1401105 has a plant height of approximately 100 cm, which is similar to 'Jazzman-2' and about 1 inch shorter than Wells. RU1401105 has an excellent straw strength, an indicator of lodging resistance, which is comparable to that of 'Roy J', 'Taggart', and Wells (based on 2016 ARPT data), and a lodging resistance better than that of Wells.

In most cases, RU1401105, like Jazzman-2 and Taggart, is moderately susceptible to common rice blast (*Pyricularia grisea* (Cooke) Sacc., races IB-1, IB-33, IB-49, IC-17, 1E-1 and IE-1K) using the standard disease ratings of R=resistant, MR=moderately resistant, MS=moderately susceptible, S=susceptible and VS=very susceptible to disease. RU1401105 is rated moderately susceptible to sheath blight (*Rhizoctonia solani* Kuhn) which compares favorably with Jazzman-2 (S), Della-2 (S), RU1401105 (MS), and Wells (S). Under high nitrogen fertilization, RU1401105 is susceptible to false smut (*Ustilaginoidea virens* (Cooke) Takah). RU1401105 is rated moderately resistant for bacterial panicle blight (*Burkholderia glumae*), as compared to Jazzman-2 (VS), Della-2 (MS), RU1401105 (S), and Taggart (MS). Reactions to straighthead, narrow brown leaf spot, stem rot, black sheath rot, and sheath spot are unknown at this time.

Rough rice grain yields of RU1401105 have been consistently exceptional in the Arkansas Rice Performance Trials (ARPT). In 19 ARPT yield trials conducted from 2014 to 2017, the average yields of RU1401105, RU1501102, 'Mermentau', Roy J, Taggart and Wells were 8221, 7616, 8322, 9028, 9230, and 8726 kg ha$^{-1}$ (120 g kg$^{-1}$ (12%) harvest moisture), respectively. In Cooperative Uniform Regional Rice Nursery (URRN) trials conducted in Arkansas, Louisiana, and Mississippi from 2014 to 2017, RU1401105 had an average grain yield of 9230 kg ha$^{-1}$, which compared favorably with those of RU151102, Jazzman-2, and Della-2 at 8020, 7868, and 8827 kg ha$^{-1}$, respectively.

Milling yields (mg g$^{-1}$ whole kernel:mg g$^{-1}$ total milled rice at 120 mg g$^{-1}$ harvest moisture) from ARPT trials conducted from 2014 to 2016, averaged 670:710, 650:690, 680:720, 650:700, 660:710, and 650:710 for RU1401105, RU1501102, Jazzman-2, Roy J, Taggart, and Wells, respectively. Milling yields from URRN trials in Arkansas conducted from 2014 to 2016 averaged 660:710, 630:680, 620:680, and 630:710 for RU1401105, Jazzman-2, 'Della-2', and Wells, respectively.

The endosperm office cultivar RU1401105 is nonglutinous, aromatic, and covered by a light brown pericarp. Rice quality parameters indicate that RU1401105 has Jasmine-type rice cooking quality characteristics as described by Webb et al. 1985, such that RU1401105 cooks like Jazzman-2. Rice cultivar RU1401105 has an average apparent starch amylase content of 16.65 g kg$^{-1}$ and a low gelatinization temperature (63.66° C.), as indicated by an average alkali (17 g kg$^{-1}$ KOH) spreading reaction of 6 to 7.

Rice cultivar RU1401105 has shown uniformity and stability as described in the following variety description information. It has been self-pollinated a sufficient number of generations with careful attention to uniformity of plant type. The variety has been increased with continued observation for uniformity. The foundation seed field of RU1401105 was rogued several times throughout the season. The variants that may be found in the release include any combination of the following: taller, shorter, earlier, later, glaborous or pubescent plants, non-aromatic, as well as intermediate or very-long slender grains. Other atypical plants may still be encountered in the variety. The total variants and/or off-types numbered less than 1 per 5,000 plants.

Rice cultivar RU1401105 has the following morphologic and other characteristics (based primarily on data collected in Stuttgart, Ark.).

TABLE 1

VARIETY DESCRIPTION INFORMATION

Plant:
Grain type: Long
Days to maturity (50% heading): 86
Plant height: 100 cm
Plant color (at booting): Green
Culm:
Angle (degrees from perpendicular after flowering):
Erect (less than 30° C)
Flag leaf (after heading):
Pubescence: Glabrous
Leaf angle (after heading): Erect
Blade color (at heading): Green
Panicle:
Length: 24.0 cm
Type: Compact
Exertion (near maturity): Moderately well
Axis: Droopy
Shattering (at maturity): Low (1%-5%)
Grain (spikelet):
Awns (after full heading): Absent
Apiculus color (at full heading): Red
Apiculus color (at maturity): Straw
Stigma color: Purple
Lemma and palea color (at maturity): Straw
Lemma and palea pubescence: Glabrous
Grain (seed):
Seed coat color: Light brown
Endosperm type: Nonglutinous
Scent: Scented
Shape class (length/width ratio):
Paddy: Long (3.4:1 and more)
Brown: Long (3.4:1 and more)
Milled: Long (3.0:1 and more)
Size: 21.7 g/1000 seeds milled rice
Starch amylose content: 16.65 g kg$^{-1}$
Alkali spreading value: 6 to 7 (17 g kg$^{-1}$ KOH Solution)
Gelatinization temperature type: Low (63.66° C.)
Disease resistance:
Rice blast (*Pyricularia grisea* (Cooke) Sacc.): Moderately susceptible
Sheath blight (*Rhizoctonia solani* Kuhn): Moderately susceptible
False smut (Ustilaginoidea virens (Cooke) Takah.): Susceptible
Bacterial panicle blight (*Burkholderia glumae*): Moderately resistant This invention also is directed to methods for producing a rice plant by crossing a first parent rice plant with a second parent rice plant wherein either the first or second parent rice plant is a rice plant of the line RU1401105. Further, both first and second parent rice plants can come from the rice cultivar RU1401105. Still further, this invention also is directed to methods for producing a rice cultivar RU1401105-derived rice plant by crossing rice cultivar RU1401105 with a second rice plant and growing the progeny seed, and repeating the crossing and growing steps with the rice cultivar RU1401105-derived plant from 0 to 7 times. Thus, any such methods using the rice cultivar RU1401105 are part of this invention: selfing, backcrosses, hybrid production, crosses to populations, and the like. All plants produced using rice cultivar RU1401105 as a parent are within the scope of this invention, including plants derived from rice cultivar RU1401105. Advantageously, the rice cultivar is used in crosses with other, different, rice cultivars to produce first generation (F1) rice seeds and plants with superior characteristics.

It should be understood that the cultivar can, through routine manipulation of cytoplasmic or other factors, be produced in a male-sterile form. Such embodiments are also contemplated within the scope of the present claims.

Transgenes or matings between plants may be useful to add specific traits to the plant and seeds provided herein. The traits may be selected for via known means for selective breeding or via available molecular biology techniques for creation and selection of transgenic plants. Transgenes conferring at least one trait selected from the group consisting of: herbicide resistance; insect resistance; resistance to bacterial, fungal, or viral disease; modified fatty acid metabolism; modified carbohydrate metabolism; and male sterility may be introduced into the plants, cells and seeds provided herein. Genes may be introduced that confer resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Transformation Techniques:

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Several methods for producing transgenic plants have been developed, and the present invention, in particular embodiments, also relates to transformed versions of the claimed cultivar.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Promega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *Proc. Natl. Acad. Sci. USA.*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.*, 5:387 (1987); Teeri, et al., *EMBO J.*, 8:343 (1989); Koncz, et al., *Proc. Natl. Acad. Sci. U.S.A.*, 84:131 (1987); DeBlock, et al., *EMBO J.*, 3:1681 (1984). Another approach to the identification of relatively rare transformation events has been use of a gene that encodes a dominant constitutive regulator of the *Zea mays* anthocyanin pigmentation pathway. Ludwig, et al., *Science*, 247:449 (1990).

In vivo methods for visualizing GUS activity that do not require destruction of plant tissue are available. Molecular Probes Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See, Ward, et al., *Plant Mol. Biol.*, 22:361-366 (1993). Exemplary inducible promoters include, but are not limited to, that from the ACEI system which responds to copper (Melt, et al., *PNAS*, 90:4567-4571 (1993)); Tn7 gene from maize which responds to benzenesulfonamide herbicide safeners (Hershey, et al., *Mol. Gen. Genetics*, 227:229-237 (1991) and Gatz, et al., *Mol. Gen. Genetics*, 243:32-38 (1994)) or Tet repressor from Tn10 (Gatz, et al., *Mol. Gen. Genetics*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena, et al., *Proc. Natl. Acad. Sci. U.S.A.*, 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989) and Christensen, et al., *Plant Mol.* 18:675-689 (1992)); pEMU (Last, et al., *Theor. Appl. Genet.*, 81:581-588 (1991)); MAS (Velten, et al., EMBO L., 3:2723-2730 (1984)); and maize H3 histone (Lepetit, et al., *Mol. Gen. Genetics*, 231:276-285 (1992) and Atanassova, et al., *Plant Journal* 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See, PCT Appl. No. WO 96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science*, 23:476-482 (1983) and Sengupta-Gopalan, et al., *Proc. Natl. Acad. Sci. USA.*, 82:3320-3324 (1985)); a leaf-specific and light-induced promoter such as that from cab or rubisco (Simpson, et al., *EMBO J.*, 4(11):2723-2729 (1985) and Timko, et al., *Nature*, 318:579-582 (1985)); an anther-specific promoter such as that from LAT52 (Twell, et al., *Mol. Gen. Genetics*, 217:240-245 (1989)); a pollen-specific promoter such as that from Zm13 (Guerrero, et al., *Mol. Gen. Genetics*, 244:161-168 (1993)) or a microspore-preferred promoter such as that from apg (Twell, et al., *Sex. Plant Reprod.*, 6:217-224 (1993)).

Signal Sequences for Targeting Proteins to Sub-Cellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Close, P. S., Master's Thesis, Iowa State University (1993); Knox, C., et al., *Plant Mol. Bial.*, 9:3-17 (1987); Lerner, et al., *Plant Physia*, 91:124-129 (1989); Fontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant J.*, 2:129 (1991); Kalderon, et al., *Cell*, 39:499-509 (1984); Steifel, et al., *Plant Cell*, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.*, 114:92-6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology*, Glick and Thompson Eds., CRC Press, Inc., Boca Raton, pp. 269-284 (1993)). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); Mindrinos, et al., *Cell*, 78:1089 (1994) (*Arabidopsis* RSP2 gene for resistance to *Pseudomonas syringae*); McDowell & Woffenden, *Trends Biotechnol.*, 21(4): 178-83 (2003); and Toyoda, et al., *Transgenic Res.*, 11 (6):567-82 (2002).

B. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, the disclosure by Van Damme, et al., *Plant Molec. Biol.*, 24:25 (1994), who disclose the nucleotide sequences of several *Clivia miniata*-mannose-binding lectin genes.

D. A vitamin-binding protein such as avidin. See, PCT Appl. No. US 93/06487. The application teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor), and Pratt, et al., *Biochem. Biophys. Res. Comm.*, 163:1243 (1989) (an allostatin is identified in *Diploptera puntata*). See also, U.S. Pat. No. 5,266, 317 to Tomalski, et al., who disclose genes encoding insect-specific, paralytic neurotoxins.

H. An insect-specific venom produced in nature by a snake, a wasp, etc. For example, see Pang, et al., *Gene*, 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Publication No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., Insect *Biochem. Molec. Biol.*, 23:691 (1993), who teach the nucleotide sequence of a cDNA encoding tobacco hornworm chitinase, and Kawalleck, et al., *Plant Molec.*

*Biol.,* 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.,* 24:757 (1994), of nucleotide sequences for mung bean calmodulin cDNA clones, and Griess, et al., *Plant Physiol.,* 104:1467 (1994), who provide the nucleotide sequence of a maize calmodulin cDNA clone.

L. A hydrophobic moment peptide. See, PCT Publication No. WO 95/16776 (disclosure of peptide derivatives of Tachyplesin which inhibit fungal plant pathogens) and PCT Publication No. WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes, et al., *Plant Sci,* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.,* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor, et al., Abstract #197, Seventh International Symposium on Molecular Plant-Microbe Interactions (Edinburgh, *Scotland* (1994)) (enzymatic inactivation in transgenic tobacco via production of single-chain antibody fragments).

P. A virus-specific antibody. See, for example, Tavladoraki, et al., *Nature,* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology,* 10:1436 (1992). The cloning and characterization of a gene which encodes a bean endopolygalacturonase-inhibiting protein is described by Toubart, et al., *Plant J.,* 2:367 (1992).

R. A developmental-arrestive protein produced in nature by a plant. For example, Logemann, et al., *Bio/Technology,* 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., *Current Biology,* 5(2) (1995); Pieterse & Van Loon, *Curr. Opin. Plant Bio.,* 7(4):456-64 (2004) and Somssich, *Cell,* 113(7):815-6 (2003).

T. Antifungal genes. See, Cornelissen and Melchers, *Plant Physiol.,* 101:709-712 (1993); Parijs, et al., *Planta,* 183:258-264 (1991) and Bushnell, et al., *Can. J. of Plant Path.,* 20(2):137-149 (1998). See also, U.S. Pat. No. 6,875,907.

U. Detoxification genes, such as for fumonisin, beauvericin, moniliformin, and zearalenone, and their structurally related derivatives. For example, see U.S. Pat. No. 5,792, 931.

V. Cystatin and cysteine proteinase inhibitors. See U.S. Pat. No. 7,205,453.

W. Defensin genes. See PCT Publication No. WO 03/000863 and U.S. Pat. No. 6,911,577.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988) and Mild, et al., *Theor. Appl. Genet.,* 80:449 (1990), respectively.

B. Glyphosate (resistance conferred by mutant 5-enolpyruvlshikirnate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Pat. Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Pat. Appl. No. 0 242 246 to Leemans, et al. DeGreef, et al., *Bio/ Technology,* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2, and Acc1-S3 genes described by Marshall, et al., *Theor. Appl. Genet.,* 83:435 (1992).

C. An herbicide that inhibits photosynthesis, such as a triazine (psbA and gs+ genes) or a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. U.S.A.,* 89:2624 (1992).

B. Decreased phytate content. 1) Introduction of a phytase-encoding gene would enhance breakdown of phytate, adding more free phosphate to the transformed plant. For example, see, Van Hartingsveldt, et al., *Gene,* 127:87 (1993), for a disclosure of the nucleotide sequence of an *Aspergillus niger* phytase gene; 2) A gene could be introduced that reduced phytate content. In maize, this, for example, could be accomplished by cloning and then reintroducing DNA associated with the single allele which is responsible for maize mutants characterized by low levels of phytic acid. See, Raboy, et al., *Maydica,* 35:383 (1990).

C. Modified carbohydrate composition effected, for example, by transforming plants with a gene coding for an enzyme that alters the branching pattern of starch. See, Shiroza, et al., *J. Bacteol.,* 170:810 (1988) (nucleotide sequence of *Streptococcus* mutants fructosyltransferase gene); Steinmetz, et al., *Mol. Gen. Genet.,* 20:220 (1985) (nucleotide sequence of *Bacillus subtilis* levansucrase gene); Pen, et al., *Bio/Technology,* 10:292 (1992) (production of transgenic plants that express *Bacillus licheniformis* α-amylase); Elliot, et al., *Plant Molec. Biol.,* 21:515 (1993) (nucleotide sequences of tomato invertase genes); Søgaard, et al., *J. Biol. Chem.,* 268:22480 (1993) (site-directed mutagenesis of barley α-amylase gene); and Fisher, et al., *Plant Physiol.,* 102:1045 (1993) (maize endospelln starch branching enzyme II).

4. Genes that Control Male Sterility:

There are several available methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. A tapetum-specific gene, RTS, a rice anther-specific gene is required for male fertility and its promoter sequence directs tissue-specific gene expression in different plant species. Luo, Hong, et. al., *Plant Molecular Biology.,* 62(3): 397-408(12) (2006). Introduction of a deacetylase gene under the control of a tapetum-specific promoter and with the application of the chemical N—Ac-PPT. See PCT Publication No. WO 01/29237.

B. Introduction of various stamen-specific promoters. Rice anther-specific promoters which are of particular utility in the production of transgenic male-sterile monocots and plants for restoring their fertility. See, U.S. Pat. No. 5,639,948. See also, PCT Publication Nos. WO 92/13956 and WO 92/13957.

C. Introduction of the bamase and the barstar genes. See, Paul, et al., *Plant Mol. Biol.,* 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et. al., "Interactions of Mitochondrial and Nuclear Genes That Affect Male Gametophyte Development," *Plant Cell.,* 16:S154-S169 (2004), all of which are hereby incorporated by reference 5. Genes that Create a Site for Site Specific DNA Integration:

This includes the introduction of FRT sites that may be used in the FLP/FRT system and/or Lox sites that may be used in the Cre/Loxp system. For example, see, Lyznik, et al., Site-Specific Recombination for Genetic Engineering in Plants, *Plant Cell Rep,* 21:925-932 (2003) and PCT Publication No. WO 99/25821, which are hereby incorporated by reference. Other systems that may be used include the Gin recombinase of phage Mu (Maeser, et al. (1991); Vicki Chandler, The Maize Handbook, ch. 118, Springer-Verlag (1994), the Pin recombinase of *E. coli* (Enomoto, et al. (1983)), and the R/RS system of the pSR1 plasmid (Araki, et al. (1992)).

6. Genes that Affect Abiotic Stress Resistance:

Genes that affect abiotic stress resistance (including, but not limited to, flowering, panicle/glume and seed development, enhancement of nitrogen utilization efficiency, altered nitrogen responsiveness, drought resistance or tolerance, cold resistance or tolerance, and salt resistance or tolerance) and increased yield under stress. For example, see: Xiong, Lizhong, et al., "Disease Resistance and Abiotic Stress Tolerance in Rice Are Inversely Modulated by an Abscisic Acid-Inducible Mitogen-Activated Protein Kinase," *The Plant Cell.,* 15:745-759 (2003), where OsMAPK5 can positively regulate drought, salt, and cold tolerance and negatively modulate PR gene expression and broad-spectrum disease resistance in rice; Chen, Fang, et. al, "The Rice 14-3-3 Gene Family and its Involvement in Responses to Biotic and Abiotic Stress," *DNA Research,* 13(2):53-63 (2006), where at least four rice GF14 genes, GF14b, GF14c, GF14e, and Gf14f, were differentially regulated by salinity, drought, wounding, and abscisic acid; PCT Publication No. WO 00/73475 where water use efficiency is altered through alteration of malate; U.S. Pat. Nos. 5,892,009, 5,965,705, 5,929,305, 5,891,859, 6,417,428, 6,664,446, 6,717,034, and 6,801,104, and PCT Publication Nos. WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publication No. 2004/0148654 and PCT Publication No. WO 01/36596 where abscisic acid is altered in plants resulting in improved plant phenotype such as increased yield and/or increased tolerance to abiotic stress; PCT Publication Nos. WO 2000/006341 and WO 04/090143, U.S. Publication No. 2004/0237147, and U.S. Pat. No. 6,992,237, where cytokinin expression is modified resulting in plants with increased stress tolerance, such as drought tolerance and/or increased yield. Also see, PCT Publication Nos. WO 02/02776, WO 2003/052063, WO 01/64898, JP 2002281975, and U.S. Pat. Nos. 6,084,153, 6,177,275, and 6,107,547 (enhancement of nitrogen utilization and altered nitrogen responsiveness). For ethylene alteration, see, U.S. Publication Nos. 2004/0128719 and 2003/0166197 and PCT Publication No. WO 2000/32761. For plant transcription factors or transcriptional regulators of abiotic stress, see, e.g., U.S. Publication Nos. 2004/0098764 and 2004/0078852.

Other genes and transcription factors that affect plant growth and agronomic traits such as yield, flowering, plant growth, and/or plant structure, can be introduced or introgressed into plants, see, e.g., PCT Publication Nos. WO 97/49811 (LHY), WO 98/56918 (ESD4), WO 97/10339, WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), and U.S. Pat. No. 6,573,430 (TFL), U.S. Pat. No. 6,713,663 (FT), U.S. Pat. Nos. 6,794,560, 6,307,126 (GAI), and PCT Publication Nos. WO 2004/076638 and WO 2004/031349 (transcription factors).

Methods for Rice Transformation

Numerous methods for plant transformation have been developed, including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993)). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Mild, et al., supra, and Moloney, et al., *Plant Cell Reports*, 8:238 (1989). See also, U.S. Pat. No. 5,591,616, issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei, et al., *The Plant Journal*, 6:271-282 (1994) and U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Technology*, 6:559-563 (1988); Sanford, J. C., *Physiol Plant*, 7:206 (1990); Klein, et al., *Biotechnology*, 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang, et al., *Bio/Technology*, 9:996 (1991). Additionally, liposome and spheroplast fusion have been used to introduce expression vectors into plants. Deshayes, et al., *EMBO J.*, 4:2731 (1985); Christou, et al., *Proc Natl. Acad. Sci. USA.*, 84:3962 (1987). Direct uptake of DNA into protoplasts using $CaCl_2$ precipitation, polyvinyl alcohol or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Bial.*, 24:51-61 (1994).

Following transformation of rice target tissues, expression of the above-described selectable marker genes allows for preferential selection of transformed cells, tissues, and/or plants using regeneration and selection methods now well known in the art.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Gene Conversion

When the term "rice plant" is used in the context of the present invention, this also includes any gene conversions of that cultivar. The teen gene converted plant as used herein refers to those rice plants which are developed by a plant breeding technique called backcrossing wherein essentially all of the desired morphological and physiological characteristics of a cultivar are recovered in addition to the one or more genes transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9, or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper (1994); Fehr (1987)). In a typical backcross protocol, the original cultivar of interest (recurrent parent) is crossed to a second cultivar (nonrecurrent parent) that carries the single gene or genes of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to one or more transferred genes from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, one or more genes of the recurrent cultivar is modified or substituted with the desired gene or genes from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic. Examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of rice and regeneration of plants therefrom is well known and widely published. For example, reference may be had to Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. No. 5,024,944, issued Jun. 18, 1991 to Collins, et al., and U.S. Pat. No. 5,008,200, issued Apr. 16, 1991 to Ranch, et al. Thus, another aspect of this invention is to provide cells which upon growth and differentiation produce rice plants having the physiological and morphological characteristics of rice variety RU1401105.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234, and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers, and the like. Thus, another aspect of this invention is to provide for cells which upon growth and differentiation produce a cultivar having essentially all of the physiological and morphological characteristics of RU1401105.

The present invention contemplates a rice plant regenerated from a tissue culture of a variety (e.g., RU1401105) or hybrid plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., "Use of bridging parents with high anther culturability to improve plant regeneration and breeding value in rice," *Rice Biotechnology Quarterly*, 38:25-26 (1999); Chu, Q. R., et al., "A novel plant regeneration medium for rice anther culture of Southern U.S. crosses," *Rice Biotechnology Quarterly*, 35:15-16 (1998); Chu, Q. R., et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J. Breed.*, 33 (S appl. 2), 306-307, illus. 1983. Thus, another aspect of this invention is to provide cells which upon growth and differentiation produce rice plants having the physiological and morphological characteristics of variety RU1401105.

Duncan, et al., *Planta*, 165:322-332 (1985), reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports*, 7:262-265 (1988), reports several media additions that enhance regenerability of callus of two cultivars. Other published reports also indicated that "non-traditional" tissues are capable of producing somatic embryogenesis and plant regeneration. K. P. Rao, et al., *Maize Genetics Cooperation Newsletter*, 60:64-65 (1986), refers to somatic embryogenesis from glume callus cultures and B. V. Conger, et al., *Plant Cell Reports*, 6:345-347 (1987), indicates somatic embryogenesis from the tissue cultures of corn leaf segments. Thus, it is clear from the literature that the state of the art is such that these methods of obtaining plants are routinely used and have a very high rate of success.

The utility of rice cultivar RU1401105 also extends to crosses with other species. Commonly, suitable species will be of the family Graminaceae, and especially of the genera *Zea*, *Tripsacum*, Croix, Schlerachne, Polytoca, Chionachne, and Trilobachne, of the tribe Maydeae.

Additional Breeding Methods

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals: The goal is to combine in a single variety an improved combination of desirable traits from the parental germplasm. These important traits may include higher seed yield, resistance to diseases and insects, better stems and roots, tolerance to low temperatures, and better agronomic characteristics or grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior crosses. The $F_1$ seed is produced by manual crosses between selected male-fertile parents or by using male sterility systems. These $F_1$s are selected for certain single gene traits such as semi-dwarf plant type, pubescence, awns, and apiculus color which indicate that the seed is truly a hybrid. Additional data on parental lines, as well as the phenotype of the $F_1$, influence the breeder's decision whether to continue with the specific cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not geminate or produce seed.

Descriptions of other breeding methods that are commonly used for different traits and crops can be found in one of several reference books (e.g., Allard, 1960; Simmonds, 1979; Sneep, et. al, 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

This invention also is directed to methods for producing a rice plant by crossing a first parent rice plant with a second parent rice plant wherein the first or second parent rice plant is a rice plant of the variety RU1401105. Further, both first and second parent rice plants can come from the rice variety RU1401105. Thus, any such methods using the rice variety RU1401105 are part of this invention: selfing, backcrosses, hybrid production, crosses to populations, and the like. All plants produced using rice variety RU1401105 as a parent are within the scope of this invention, including those developed from varieties derived from rice variety RU1401105. Advantageously, the rice variety could be used in crosses with other, different, rice plants to produce the first generation ($F_1$) rice hybrid seeds and plants with superior characteristics. The variety of the invention can also be used for transformation where exogenous genes are introduced and expressed by the variety of the invention. Genetic variants created either through traditional breeding methods using variety RU1401105 or through transformation of RU1401105 by any of a number of protocols known to those of skill in the art are intended to be within the scope of this invention.

The following describes breeding methods that may be used with cultivar RU1401105 in the development of further rice plants. One such embodiment is a method for developing a RU1401105 progeny rice plant in a rice plant breeding program comprising: obtaining the rice plant, or a part thereof, of cultivar RU1401105 utilizing said plant or plant part as a source of breeding material and selecting a RU1401105 progeny plant with molecular markers in common with RU1401105 and/or with morphological and/or physiological characteristics selected from the characteristics listed in Tables 2 or 3. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar RU1401105 progeny rice plants, comprising crossing cultivar RU1401105 with another rice plant, thereby producing a population of rice plants, which, on average, derive 50% of their alleles from cultivar RU1401105. A plant of this population may be selected and repeatedly selfed or sibbed with a rice cultivar resulting from these successive filial generations. One embodiment of this invention is the rice cultivar produced by this method and that has obtained at least 50% of its alleles from cultivar RU1401105.

One of ordinary skill in the art of plant breeding would know how to evaluate the traits of two plant varieties to determine if there is no significant difference between the two traits expressed by those varieties. For example, see, Fehr and Walt, Principles of Cultivar Development, pp. 261-286 (1987). Thus the invention includes rice cultivar RU1401105 progeny rice plants comprising a combination of at least two RU1401105 traits selected from the group consisting of those listed in the Tables herein, or the RU1401105 combination of traits listed in the Summary of the Invention, so that said progeny rice plant is not significantly different for said traits than rice cultivar RU1401105 as determined at the 5% significance level when grown in the same environment. Using techniques described herein, molecular markers may be used to identify said progeny plant as a RU1401105 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice cultivar RU1401105 may also be characterized through their filial relationship with rice cultivar RU1401105, as for example, being within a certain number of breeding crosses office cultivar RU1401105. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar RU1401105 and its progeny. For example, progeny produced by the methods described herein may be within 1, 2, 3, 4, or 5 breeding crosses of rice cultivar RU1401105.

Pedigree Breeding

The seed of rice cultivar RU1401105, the plant produced from the cultivar seed, the hybrid rice plant produced from the crossing of the cultivar, hybrid seed, and various parts of the hybrid rice plant and transgenic versions of the foregoing, can be utilized for human food, livestock feed, and as a raw material in industry.

In Table 2, agronomic characteristics are shown for rice cultivar RU1401105 and for eight other rice cultivars. These data are the result of the Arkansas Rice Performance Trials (ARPT) conducted in 2014. (Stuttgart, Rice Research and Extension Center (RREC); Colt, Pine Tree Branch Experiment Station (PTES); Clay Co.; and Desha Co.). Column one shows the variety, column two shows the yield in bushels per acre, column three shows the plant height in inches, column four shows the maturity in days to 50% heading, column five shows the kernel weight in milligrams and column six shows the milling percent head rice (or whole kernel rice) as compared to the percent of total milled rice. Milling data collected from RREC, PTES, Clay Co., and Desha Co. test plots.

TABLE 2

| VARIETY | YIELD (BU/AC) | HEIGHT (IN.) | MATURITY (50% HD) | KERNEL WT (mg)* | MILLING HR:TOT* |
|---|---|---|---|---|---|
| RU1401105 | 173 | 39.5 | 87 | 21.5 | 69:72 |
| RU1501102 | 141 | 37.6 | 89 | 23.1 | 66:70 |
| Jazzman-2 | 171 | 39.1 | 87 | 21.3 | 68:71 |
| CL Jazzman | 164 | 39.5 | 88 | 22.2 | 67:71 |
| Antonio | 172 | 36.5 | 86 | 19.8 | 69:72 |
| Mermentau | 176 | 37.4 | 86 | 19.5 | 68:71 |
| Roy J | 186 | 41.3 | 90 | 21.0 | 66:71 |
| Taggart | 206 | 43.1 | 89 | 22.1 | 67:71 |
| Wells | 181 | 41.7 | 88 | 21.3 | 65:72 |

In Table 3, agronomic characteristics are shown for rice cultivar RU1401105 and for six other rice cultivars. These data are the result of the Arkansas Rice Performance Trials (ARPT) conducted in 2015. (Stuttgart, Rice Research and Extension Center (RREC); Keiser, Northeast Research and Extension Center (NEREC); Colt, Pine Tree Branch Experiment Station (PTES); Clay Co.; and Desha Co.). Column one shows the variety, column two shows the yield in bushels per acre, column three shows the plant height in inches, column four shows the maturity in days to 50% heading, column five shows the kernel weight in milligrams and column six shows the milling percent head rice (or whole kernel rice) as compared to the percent of total milled rice. Milling data collected from RREC, NEREC, PTES, NES, and Clay Co. test plots.

TABLE 3

| VARIETY | YIELD (BU/AC) | HEIGHT (IN.) | MATURITY (50% HD) | KERNEL WT (mg)* | MILLING HR:TOT* |
|---|---|---|---|---|---|
| RU1401105 | 142 | 37.3 | 78 | 22.0 | 69:72 |
| RU1501102 | 138 | 35.8 | 79 | 24.1 | 65:70 |
| Antonio | 141 | 36.5 | 75 | 20.5 | 68:71 |
| Mermentau | 161 | 37.0 | 76 | 20.5 | 67:70 |
| Roy J | 169 | 39.1 | 81 | 20.6 | 65:71 |
| Taggart | 167 | 41.4 | 82 | 22.9 | 66:72 |
| Wells | 161 | 38.7 | 78 | 21.8 | 67:72 |

In Table 4, agronomic characteristics are shown for rice cultivar RU1401105 and for five other rice cultivars. These data are the result of the Arkansas Rice Performance Trials (ARPT) conducted in 2016. (Stuttgart, Rice Research and Extension Center (RREC); Keiser, Northeast Research and Extension Center (NEREC); Colt, Pine Tree Branch Experiment Station (PTES); Newport, (NES); and Clay Co.). Column one shows the variety, column two shows the yield in bushels per acre, column three shows the plant height in inches, column four shows the maturity in days to 50% heading, column five shows the kernel weight in milligrams and column six shows the milling percent head rice (or whole kernel rice) as compared to the percent of total milled rice. Milling data collected from RREC, NEREC, PTES, NES, and Clay Co. test plots.

TABLE 4

| VARIETY | YIELD (BU/AC) | HEIGHT (IN.) | MATURITY (50% HD) | KERNEL WT (mg)* | MILLING HR:TOT* |
|---|---|---|---|---|---|
| RU1401105 | 162 | 41.6 | 84 | 21.6 | 65:69 |
| RU1501102 | 147 | 38.8 | 86 | 22.6 | 63:68 |
| Mermentau | 159 | 40.3 | 85 | 20.0 | 64:68 |
| Roy J | 167 | 43.6 | 90 | 20.5 | 63:69 |
| Taggart | 179 | 45.4 | 88 | 23.1 | 65:70 |
| Wells | 171 | 42.7 | 85 | 22.5 | 62:69 |

In Table 5, agronomic characteristics are shown for rice cultivar RU1401105 and for four other rice cultivars. These data are the result of the Arkansas Rice Performance Trials (ARPT) conducted in 2017. (Stuttgart, Rice Research and Extension Center (RREC); Keiser, Northeast Research and Extension Center (NEREC); Colt, Pine Tree Branch Experiment Station (PTES); Clay Co.; and Desha Co.). Column one shows the variety, column two shows the yield in bushels per acre, column three shows the plant height in inches, and column four shows the maturity in days to 50% heading. Kernel weight and milling data not available as of November, 2017.

TABLE 5

| VARIETY | YIELD (BU/AC) | HEIGHT (IN.) | MATURITY (50% HD) | KERNEL WT (mg)* | MILLING HR:TOT* |
|---|---|---|---|---|---|
| RU1401105 | 176 | 42.1 | 92 | | |
| RU1501102 | 177 | 41.3 | 91 | | |
| Roy J | 196 | 42.1 | 94 | | |
| Taggart | 183 | 46.0 | 94 | | |
| Wells | 182 | 42.5 | 91 | | |

In Table 6, agronomic characteristics are shown for rice cultivar RU1401105 and for eight other rice cultivars. These data are the mean of the Arkansas Rice Performance Trials (ARPT) conducted in 2014-2017. (Stuttgart, Rice Research and Extension Center (RREC); Keiser, Northeast Research and Extension Center (NEREC); Colt, Pine Tree Branch Experiment Station (PTES); Newport, (NES); Clay Co.; and Desha Co.). Column one shows the variety, column two shows the average yield in bushels per acre, column three shows the average plant height in inches, column four shows the average maturity in days to 50% heading, column five shows the average kernel weight in milligrams and column six shows the average milling percent head rice (or whole kernel rice) as compared to the percent of total milled rice. Milling data collected from RREC in 2014, 2015, 2016; NEREC in 2015, 2016; NES in 2016; PTES in 2014, 2015, 2016; Clay County in 2014, 2015, 2016; and Desha County in 2014, 2015. Note: Jazzman-2 and CL Jazzman data presented from one year only (2014). Antonio data presented from two years (2014 and 2015). Mermentau and RU1501102 data presented from three years (2014, 2015, and 2016).

TABLE 6

| VARIETY | YIELD (BU/AC) | HEIGHT (IN.) | MATURITY (50% HD) | KERNEL WT (MG)* | MILLING HR:TOT* |
|---|---|---|---|---|---|
| RU1401105 | 163 | 39.8 | 86 | 21.7 | 67:71 |
| RU1501102# | 151 | 38.1 | 87 | 23.3 | 65:69 |
| Jazzman-2# | 171 | 39.2 | 87 | 21.3 | 68:72 |
| CL Jazzman# | 164 | 39.4 | 88 | 22.2 | 67:71 |
| Antonio# | 155 | 36.5 | 81 | 20.0 | 69:71 |
| Mermentau# | 165 | 38.3 | 83 | 20.0 | 67:70 |
| Roy J | 179 | 41.6 | 89 | 20.7 | 65:70 |
| Taggart | 183 | 43.8 | 88 | 22.7 | 66:71 |
| Wells | 173 | 41.5 | 86 | 21.7 | 65:71 |

In Table 7, agronomic characteristics are shown for rice cultivar RU1401105 and for eight other rice cultivars. The data are the result of trials at the Arkansas Rice Performance Trials (ARPT) from 2014 by location, including Stuttgart, Rice Research and Extension Center (RREC); Colt, Pine Tree Branch Experiment Station (PTES); Clay Co. (CL CO); and Desha Co. (DE CO). Column one shows the variety, columns two to five give the average grain yield for each of 4 different locations for each variety in bushels per acre, column six shows the average grain yield for the 4 locations, columns seven to ten show the average head rice (%) to total rice (%) ratio for each of 4 different locations and column eleven shows the average head rice (%) to total rice (%) ratio for the 4 locations.

TABLE 7

| | GRAIN YIELD (BU/AC) | | | | | HEAD RICE(%):TOTAL RICE(%) | | | | |
|---|---|---|---|---|---|---|---|---|---|---|
| VARIETY | RREC | PTES | CL CO | DE CO | AVG | RREC | PTES | CL CO | DE CO | AVG |
| RU1401105 | 175 | 177 | 171 | 167 | 173 | 70:73 | 69:71 | 68:72 | 69:71 | 69:72 |
| RU1501102 | 138 | 142 | 153 | 128 | 141 | 67:70 | 66:74 | 67:71 | 65:68 | 66:70 |
| Jazzman-2 | 159 | 179 | 168 | 177 | 171 | 69:72 | 66:71 | 66:72 | 69:71 | 68:71 |
| CLJazzman | 160 | 167 | 153 | 174 | 164 | 68:71 | 65:70 | 66:70 | 69:71 | 67:71 |
| Antonio | 152 | 169 | 174 | 195 | 176 | 70:71 | 69:72 | 68:71 | 71:72 | 69:72 |
| Mermentau | 158 | 177 | 179 | 190 | 181 | 70:72 | 68:71 | 67:71 | 69:71 | 68:71 |
| Roy J | 178 | 197 | 208 | 160 | 172 | 67:72 | 66:71 | 65:72 | 65:68 | 66:71 |
| Taggart | 168 | 189 | 213 | 177 | 169 | 68:71 | 66:72 | 65:72 | 68:69 | 67:71 |
| Wells | 171 | 181 | 196 | 177 | 186 | 67:72 | 62:72 | 61:72 | 69:72 | 65:72 |

In Table 8, starch-related properties are shown for rice cultivar RU1401105 and for eight other rice cultivars. The data are the result of trials at the Arkansas Rice Performance Trials (ARPT) from 2014 by location, including Stuttgart, Rice Research and Extension Center (RREC); Colt, Pine Tree Branch Experiment Station (PTES); Clay Co. (CL CO); and Desha Co. (DE CO). Column one shows the variety, columns two to five give the average apparent starch amylose content for each of 4 different locations for each variety in g kg$^{-1}$, column six shows the average apparent starch amylose content for the 4 locations, columns seven to ten show the average gelatinization temperature for each of 4 different locations in degrees Celsius and column eleven shows the average gelatinization temperature for the 4 locations.

TABLE 8

| | AMYLOSE | | | | | GEL TEMP | | | | |
|---|---|---|---|---|---|---|---|---|---|---|
| VARIETY | RREC | PTES | CL CO | DE CO | AVG | RREC | PTES | CL CO | DE CO | AVG |
| RU1401105 | 17.27 | 14.86 | 15.59 | 14.46 | 15.77 | 62.28 | 63.94 | 63.10 | 62.71 | 63.62 |
| RU1501102 | 19.25 | 16.36 | 17.35 | 16.91 | 17.87 | 63.14 | 63.67 | 62.39 | 63.54 | 63.22 |
| Jazzman-2 | 16.91 | 14.59 | 15.83 | 15.09 | 15.61 | 61.72 | 64.55 | 64.60 | 66.09 | 64.24 |
| CLJazzman | 17.44 | 14.27 | 15.88 | 14.35 | 15.48 | 62.21 | 64.91 | 63.77 | 62.47 | 63.34 |
| Antonio | 21.62 | 20.70 | 21.43 | 21.75 | 21.32 | 70.64 | 70.74 | 71.30 | 70.21 | 70.79 |
| Mermentau | 22.83 | 21.94 | 22.34 | 22.40 | 23.38 | 70.14 | 69.90 | 69.12 | 67.44 | 69.15 |
| Roy J | 23.28 | 22.81 | 22.85 | 22.48 | 22.86 | 69.80 | 69.68 | 67.90 | 70.69 | 69.52 |
| Taggart | 21.61 | 22.29 | 24.11 | 22.30 | 22.58 | 69.00 | 68.73 | 68.04 | 69.42 | 68.80 |
| Wells | 21.52 | 18.65 | 21.79 | 21.64 | 20.90 | 69.48 | 66.81 | 69.70 | 70.07 | 69.01 |

In Table 9, agronomic characteristics are shown for rice cultivar RU1401105 and for six other rice cultivars. The data are the result of trials at the Arkansas Rice Performance Trials (ARPT) from 2015 by location, including Stuttgart, Rice Research and Extension Center (RREC); Keiser, Northeast Research and Extension Center (NEREC); Colt, Pine Tree Branch Experiment Station (PTES); Clay Co. (CL CO); and Desha Co. (DE CO). Column one shows the variety, columns two to six give the average grain yield for each of 5 different locations for each variety in bushels per acre, column seven shows the average grain yield for the 5 locations.

TABLE 9

| | GRAIN YIELD (BU/AC) | | | | | |
|---|---|---|---|---|---|---|
| VARIETY | RREC | NEREC | PTES | CLAY CO | DESHA CO | AVG |
| RU1401105 | 120 | 182 | 146 | 139 | 122 | 142 |
| RU1501102 | 123 | 152 | 141 | 146 | 126 | 138 |

TABLE 9-continued

| | GRAIN YIELD (BU/AC) | | | | | |
|---|---|---|---|---|---|---|
| VARIETY | RREC | NEREC | PTES | CLAY CO | DESHA CO | AVG |
| Antonio | 118 | 166 | 122 | 162 | 139 | 141 |
| Mermentau | 137 | 187 | 140 | 174 | 167 | 161 |
| Roy J | 146 | 195 | 170 | 182 | 149 | 169 |
| Taggart | 143 | 194 | 159 | 182 | 157 | 167 |
| Wells | 131 | 182 | 165 | 179 | 149 | 161 |

In Table 10, agronomic characteristics are shown for rice cultivar RU1401105 and for six other rice cultivars. The data are the result of trials at the Arkansas Rice Performance Trials (ARPT) from 2015 by location, including Stuttgart, Rice Research and Extension Center (RREC); Keiser, Northeast Research and Extension Center (NEREC); Colt, Pine Tree Branch Experiment Station (PTES); Clay Co. (CL CO); and Desha Co. (DE CO). Column one shows the variety, columns two to six show the average head rice (%) to total rice (%) ratio for each of 5 different locations for each variety and column seven shows the average head rice (%) to total rice (%) ratio for the 5 locations.

TABLE 10

HEAD RICE(%):TOTAL RICE(%)

| VARIETY | RREC | NEREC | PTES | CLAY CO | DESHA CO | AVG |
|---|---|---|---|---|---|---|
| RU1401105 | 71:73 | 68:71 | 65:71 | 70:72 | No Data | 69:72 |
| RU1501102 | 67:70 | 65:69 | 60:70 | 68:71 | 66:70 | 65:70 |
| Antonio | No Data | 67:70 | No Data | 69:72 | 65:72 | 68:71 |
| Mermentau | 66:70 | 67:70 | 65:69 | 69:72 | 66:70 | 67:70 |
| Roy J | 65:70 | 66:70 | 65:70 | 67:71 | 62:71 | 65:71 |
| Taggart | 66:72 | 67:70 | 64:72 | 68:72 | 67:72 | 66:72 |
| Wells | 68:72 | 69:72 | 59:72 | 69:73 | 65:70 | 67:72 |

In Table 11, starch-related properties are shown for rice cultivar RU1401105 and for six other rice cultivars. The data are the result of trials at the Arkansas Rice Performance Trials (ARPT) from 2015 by location, including Stuttgart, Rice Research and Extension Center (RREC); Keiser, Northeast Research and Extension Center (NEREC); Colt, Pine Tree Branch Experiment Station (PTES); Clay Co. (CL CO); and Desha Co. (DE CO). Column one shows the variety, columns two to six show the average apparent starch amylose content for each of 5 different locations for each variety in g kg$^{-1}$ and column seven shows the average apparent starch amylose content for the 5 locations.

TABLE 11

AMYLOSE

| VARIETY | RREC | NEREC | PTES | CLAY CO | DESHA CO | AVG |
|---|---|---|---|---|---|---|
| RU1401105 | 15.93 | 17.08 | 19.44 | 17.67 | No Data | 17.48 |
| RU1501102 | 18.96 | 18.38 | 22.02 | 19.77 | 19.58 | 19.74 |
| Antonio | No Data | 22.13 | No Data | 24.24 | 21.59 | 23.05 |
| Mermentau | 23.36 | 22.82 | 24.80 | 23.13 | 18.62 | 22.46 |
| Roy J | 21.72 | 22.30 | 25.10 | 22.88 | 23.00 | 23.00 |
| Taggart | 23.15 | 21.49 | 24.37 | 23.15 | 21.87 | 22.81 |
| Wells | 21.28 | 21.73 | 23.18 | 22.63 | 22.81 | 22.28 |

In Table 12, starch-related properties are shown for rice cultivar RU1401105 and for six other rice cultivars. The data are the result of trials at the Arkansas Rice Performance Trials (ARPT) from 2015 by location, including Stuttgart, Rice Research and Extension Center (RREC); Keiser, Northeast Research and Extension Center (NEREC); Colt, Pine Tree Branch Experiment Station (PTES); Clay Co. (CL CO); and Desha Co. (DE CO). Column one shows the variety, columns two to six show the average gelatinization temperature for each of 5 different locations for each variety in degrees Celsius and column seven shows the average gelatinization temperature for the 5 locations.

TABLE 12

GEL TEMP

| VARIETY | RREC | NEREC | PTES | CLAY CO | DESHA CO | AVG |
|---|---|---|---|---|---|---|
| RU1401105 | 63.97 | 62.31 | 61.52 | 62.70 | No Data | 62.58 |
| RU1501102 | 62.54 | 63.11 | 61.48 | 60.52 | 61.97 | 61.92 |
| Antonio | No Data | 69.89 | No Data | 69.10 | 69.54 | 69.41 |
| Mermentau | 70.77 | 69.15 | 68.38 | 69.05 | 65.34 | 68.29 |
| Roy J | 69.44 | 68.76 | 67.12 | 68.38 | 68.95 | 68.53 |
| Taggart | 70.05 | 68.41 | 66.41 | 67.22 | 67.49 | 67.92 |
| Wells | 69.86 | 67.79 | 66.35 | 68.96 | 70.13 | 68.55 |

In Table 13, agronomic characteristics are shown for rice cultivar RU1401105 and for five other rice cultivars. The data are the result of trials at the Arkansas Rice Performance Trials (ARPT) from 2016 by location, including Stuttgart, Rice Research and Extension Center (RREC); Keiser, Northeast Research and Extension Center (NEREC); Colt, Pine Tree Branch Experiment Station (PTES); Newport, (NES); and Clay Co. (CL CO). Column one shows the variety, columns two to six give the average grain yield for each of 5 different locations for each variety in bushels per acre, column seven shows the average grain yield for the 5 locations.

TABLE 13

GRAIN YIELD (BU/AC)

| VARIETY | RREC | NEREC | PTES | NES | CLAY CO | AVG |
|---|---|---|---|---|---|---|
| RU1401105 | 169 | 173 | 156 | 138 | 177 | 162 |
| RU1501102 | 144 | 148 | 138 | 124 | 181 | 147 |
| Mermentau | 169 | 181 | 148 | 125 | 173 | 159 |
| Roy J | 159 | 187 | 164 | 135 | 191 | 167 |
| Taggart | 186 | 197 | 170 | 147 | 193 | 179 |
| Wells | 170 | 189 | 152 | 150 | 194 | 171 |

In Table 14, agronomic characteristics are shown for rice cultivar RU1401105 and for five other rice cultivars. The data are the result of trials at the Arkansas Rice Performance Trials (ARPT) from 2016 by location, including Stuttgart, Rice Research and Extension Center (RREC); Keiser, Northeast Research and Extension Center (NEREC); Colt, Pine Tree Branch Experiment Station (PTES); Newport, (NES); and Clay Co. (CL CO). Column one shows the variety, columns two to six show the average head rice (%) to total rice (%) ratio for each of 5 different locations for each variety and column seven shows the average head rice (%) to total rice (%) ratio for the 5 locations.

TABLE 14

HEAD RICE(%):TOTAL RICE(%)

| VARIETY | RREC | NEREC | PTES | NES | CLAY CO | AVG |
|---|---|---|---|---|---|---|
| RU1401105 | 69:69 | 66:70 | 62:67 | 62:70 | 64:69 | 65:69 |
| RU1501102 | 66:68 | 62:67 | 57:64 | 64:69 | 65:70 | 63:68 |
| Mermentau | 64:68 | 65:68 | 61:66 | No Data | 65:68 | 64:68 |
| Roy J | 66:69 | 64:69 | 58:66 | No Data | 64:70 | 63:69 |
| Taggart | 66:71 | 66:71 | 61:69 | No Data | 65:69 | 65:70 |
| Wells | 66:67 | 65:70 | 57:67 | No Data | 62:70 | 62:69 |

In Table 15, starch-related properties are shown for rice cultivar RU1401105 and for five other rice cultivars. The data are the result of trials at the Arkansas Rice Performance Trials (ARPT) from 2016 by location, including Stuttgart, Rice Research and Extension Center (RREC); Keiser, Northeast Research and Extension Center (NEREC); Colt, Pine Tree Branch Experiment Station (PTES); Newport, (NES); and Clay Co. (CL CO). Column one shows the variety, columns two to six show the average apparent starch amylose content for each of 5 different locations for each variety in g kg$^{-1}$ and column seven shows the average apparent starch amylose content for the 5 locations.

TABLE 15

AMYLOSE

| VARIETY | RREC | NEREC | PTES | NES | CLAY CO | AVG |
|---|---|---|---|---|---|---|
| RU1401105 | 18.50 | 17.33 | 15.38 | 15.31 | 16.94 | 16.69 |
| RU1501102 | 17.34 | 17.68 | 16.18 | 16.65 | 18.67 | 17.30 |
| Mermentau | 21.51 | 23.19 | 21.13 | No Data | 22.8 | 22.16 |
| Roy J | 20.88 | 23.00 | 20.96 | No Data | 23.58 | 22.11 |
| Taggart | 21.63 | 24.17 | 21.47 | No Data | 22.79 | 22.52 |
| Wells | 20.96 | 21.19 | 21.54 | No Data | 22.62 | 21.58 |

In Table 16, starch-related properties are shown for rice cultivar RU1401105 and for five other rice cultivars. The data are the result of trials at the Arkansas Rice Performance Trials (ARPT) from 2016 by location, including Stuttgart, Rice Research and Extension Center (RREC); Keiser, Northeast Research and Extension Center (NEREC); Colt, Pine Tree Branch Experiment Station (PTES); Newport, (NES); and Clay Co. (CL CO). Column one shows the variety, columns two to six show the average gelatinization temperature for each of 5 different locations for each variety in degrees Celsius and column seven shows the average gelatinization temperature for the 5 locations.

TABLE 16

GEL TEMP

| VARIETY | RREC | NEREC | PTES | NES | CLAY CO | AVG |
|---|---|---|---|---|---|---|
| RU1401105 | 67.63 | 63.39 | 64.47 | 64.08 | 64.29 | 64.77 |
| RU1501102 | 67.09 | 63.89 | 64.89 | 64.59 | 64.85 | 65.06 |
| Mermentau | 73.07 | 72.97 | 72.07 | No Data | 72.14 | 72.56 |
| Roy J | 72.29 | 71.93 | 71.80 | No Data | 71.55 | 71.89 |
| Taggart | 72.14 | 70.94 | 71.17 | No Data | 71.85 | 71.53 |
| Wells | 73.76 | 71.43 | 71.46 | No Data | 72.12 | 72.19 |

In Table 17, agronomic characteristics are shown for rice cultivar RU1401105 and for four other rice cultivars. The data are the result of trials at the Arkansas Rice Performance Trials (ARPT) from 2017 by location, including Stuttgart, Rice Research and Extension Center (RREC); Keiser, Northeast Research and Extension Center (NEREC); Colt, Pine Tree Branch Experiment Station (PTES); Clay Co. (CL CO); and Desha Co. (DE CO). Column one shows the variety, columns two to six give the average grain yield for each of 5 different locations for each variety in bushels per acre, column seven shows the average grain yield for the 5 locations.

TABLE 17

GRAIN YIELD (BU/AC)

| VARIETY | RREC | NEREC | PTES | CLAY CO | DESHA CO | AVG |
|---|---|---|---|---|---|---|
| RU1401105 | 162 | 168 | 169 | 197 | 185 | 176 |
| RU1501102 | 158 | 173 | 179 | 193 | 182 | 177 |
| Roy J | 197 | 186 | 184 | 209 | 205 | 196 |
| Taggart | 182 | 184 | 177 | 190 | 184 | 183 |
| Wells | 166 | 191 | 164 | 191 | 196 | 182 |

In Table 18, agronomic characteristics are shown for rice cultivar RU1401105 and for eight other rice cultivars. The data are the mean of the Arkansas Rice Performance Trials (ARPT) conducted in 2014-2017 by location, including Stuttgart, Rice Research and Extension Center (RREC); Keiser, Northeast Research and Extension Center (NEREC); Colt, Pine Tree Branch Experiment Station (PTES); Newport, (NES); Clay Co. (CL CO); and Desha Co. (DE CO). Column one shows the variety, columns two to seven give the average grain yield for each of 6 different locations for each variety in bushels per acre, column eight shows the average grain yield for the 6 locations. Note: Grain Yield data collected from RREC in 2014, 2015, 2016, 2017; NEREC in 2015, 2016, 2017; PTES in 2014, 2015, 2016, 2017; NES in 2016; Clay County in 2014, 2015, 2016, 2017; and Desha County in 2014, 2015, 2017.

TABLE 18

GRAIN YIELD (BU/AC)

| VARIETY | RREC | NEREC | PTES | NES | Clay Co. | Desha Co. | AVG |
|---|---|---|---|---|---|---|---|
| RU1401105 | 157 | 174 | 162 | 138 | 171 | 158 | 163 |
| RU1501102 | 141 | 158 | 150 | 124 | 168 | 145 | 151 |
| Jazzman-2 | 159 | No Data | 179 | No Data | 168 | 177 | 171 |
| CL Jazzman | 160 | No Data | 167 | No Data | 153 | 174 | 164 |
| Antonio | 135 | 166 | 146 | No Data | 168 | 167 | 155 |
| Mermentau | 155 | 184 | 155 | 125 | 175 | 179 | 165 |
| Roy J | 170 | 189 | 179 | 135 | 198 | 171 | 179 |
| Taggart | 170 | 192 | 174 | 147 | 195 | 173 | 183 |
| Wells | 160 | 187 | 166 | 150 | 190 | 174 | 173 |

In Table 19, agronomic characteristics are shown for rice cultivar RU1401105 and for eight other rice cultivars. The data are the mean of the Arkansas Rice Performance Trials (ARPT) conducted in 2014-2016 by location, including Stuttgart, Rice Research and Extension Center (RREC); Keiser, Northeast Research and Extension Center (NEREC); Colt, Newport, (NES); Pine Tree Branch Experiment Station (PTES); Clay Co. (CL CO); and Desha Co. (DE CO). Column one shows the variety, columns two to seven give the average head rice (%) to total rice (%) ratio for each of 6 different locations for each variety and column eight shows the average head rice (%) to total rice (%) ratio for the 6 locations. Milling data was collected from RREC in 2014, 2015, 2016; NEREC in 2015, 2016; NES in 2016; PTES in 2014, 2015, 2016; Clay County in 2014, 2015, 2016; and Desha County in 2014, 2015.

TABLE 19

HEAD RICE(%):TOTAL RICE(%)

| VARIETY | RREC | NEREC | NES | PTES | Clay Co. | Desha Co. | AVG |
|---|---|---|---|---|---|---|---|
| RU1401105 | 70:72 | 67:71 | 62:70 | 65:70 | 67:71 | 69:71 | 67:71 |
| RU1501102 | 67:69 | 64:68 | 64:69 | 61:69 | 67:71 | 66:69 | 65:69 |
| Jazzman-2 | 69:72 | No Data | No Data | 66:71 | 66:72 | 69:71 | 68:72 |
| CL Jazzman | 68:71 | No Data | 65:70 | 66:70 | 69:71 | 67:71 | |
| Antonio | 70:71 | 67:70 | No Data | 69:72 | 69:72 | 68:72 | 69:71 |
| Mermentau | 67:70 | 66:69 | No Data | 65:69 | 67:70 | 68:71 | 67:70 |
| Roy J | 66:70 | 65:70 | No Data | 63:69 | 65:71 | 64:70 | 65:70 |
| Taggart | 67:71 | 67:71 | No Data | 64:71 | 66:71 | 68:71 | 66:71 |
| Wells | 67:70 | 67:71 | No Data | 59:70 | 64:72 | 67:71 | 65:71 |

In Table 20, agronomic characteristics are shown for rice cultivar RU1401105 and for four other rice cultivars. The data are the result of trials at the Cooperative Uniform Regional Rice Nursery (URRN) conducted in 2014. Column one shows the variety, column two shows the grain yield in bushels per acre, column three shows the height in inches, column four shows the maturity in number of days from emergence to 50% heading, and column five gives the milling percent head rice (or whole kernel rice) as compared to the percent of total milled rice.

TABLE 20

| VARIETY | YIELD (BU/AC) | HEIGHT (IN.) | MATURITY (50% HD) | MILLING HR:TOT |
|---|---|---|---|---|
| RU1401105 | 213 | 39.4 | 87 | 70:72 |
| Jazzman-2 | 175 | 37.0 | 83 | 69:72 |
| Della-2 | 175 | 40.2 | 87 | 68:71 |
| Mermentau | 221 | 37.8 | 87 | 70:73 |
| Wells | 251 | 41.3 | 85 | 69:74 |

In Table 21, agronomic characteristics are shown for rice cultivar RU1401105 and for five other rice cultivars. The data are the result of trials at the Cooperative Uniform Regional Rice Nursery (URRN) conducted in 2015. Column one shows the variety, column two shows the grain yield in bushels per acre, column three shows the height in inches, column four shows the maturity in number of days from emergence to 50% heading, and column five gives the milling percent head rice (or whole kernel rice) as compared to the percent of total milled rice.

TABLE 21

| VARIETY | YIELD (BU/AC) | HEIGHT (IN.) | MATURITY (50% HD) | MILLING HR:TOT |
|---|---|---|---|---|
| RU1401105 | 174 | 43.3 | 97 | 67:70 |
| RU1501102 | 152 | 40.9 | 100 | 64:69 |
| Jazzman-2 | 149 | 35.0 | 96 | 66:69 |
| Della-2 | 172 | 43.3 | 100 | 65:68 |
| Mermentau | 202 | 41.3 | 98 | 67:71 |
| Wells | 189 | 44.9 | 100 | 65:70 |

In Table 22, agronomic characteristics are shown for rice cultivar RU1401105 and for five other rice cultivars. The data are the result of trials at the Cooperative Uniform Regional Rice Nursery (URRN) conducted in 2016. Column one shows the variety, column two shows the grain yield in bushels per acre, column three shows the height in inches, column four shows the maturity in number of days from emergence to 50% heading, and column five gives the milling percent head rice (or whole kernel rice) as compared to the percent of total milled rice.

TABLE 22

| VARIETY | YIELD (BU/AC) | HEIGHT (IN.) | MATURITY (50% HD) | MILLING HR:TOT |
|---|---|---|---|---|
| RU1401105 | 139 | 42.5 | 88 | 61:69 |
| RU1501102 | 106 | 40.6 | 87 | 55:65 |
| Jazzman-2 | 115 | 39.0 | 86 | 55:63 |
| Della-2 | 137 | 44.5 | 89 | 57:64 |
| Mermentau | 125 | 42.1 | 87 | 56:67 |
| Wells | 162 | 47.2 | 87 | 60:70 |

In Table 23, agronomic characteristics are shown for rice cultivar RU1401105 and for five other rice cultivars. The data are the result of trials at the Cooperative Uniform Regional Rice Nursery (URRN) conducted in 2017. Column one shows the variety, column two shows the grain yield in bushels per acre, column three shows the height in inches, column four shows the maturity in number of days from emergence to 50% heading, and column five gives the milling percent head rice (or whole kernel rice) as compared to the percent of total milled rice.

TABLE 23

| VARIETY | YIELD (BU/AC) | HEIGHT (IN.) | MATURITY (50% HD) | MILLING HR:TOT |
|---|---|---|---|---|
| RU1401105 | 162 | 41.3 | 86 | 66:71 |
| RU1501102 | 172 | 41.3 | 85 | 65:69 |
| Jazzman-2 | 137 | 33.9 | 82 | 62:67 |
| Della-2 | 165 | 41.3 | 86 | 58:67 |
| Mermentau | 197 | 38.1 | 81 | 61:71 |
| Wells | 209 | 42.9 | 81 | 59:71 |

In Table 24, agronomic characteristics are shown for rice cultivar RU1401105 and for five other rice cultivars. The data are the mean from the Cooperative Uniform Regional Rice Nursery (URRN) trials conducted in 2014-2017. Column one shows the variety, column two shows the grain yield in bushels per acre, column three shows the height in inches, column four shows the maturity in number of days from emergence to 50% heading, and column five gives the milling percent head rice (or whole kernel rice) as compared to the percent of total milled rice.

TABLE 24

| VARIETY | YIELD (BU/AC) | HEIGHT (IN.) | MATURITY (50% HD) | MILLING HR:TOT |
|---|---|---|---|---|
| RU1401105 | 172 | 41.6 | 90 | 66:71 |
| RU1501102 | 143 | 40.9 | 91 | 61:68 |
| Jazzman-2 | 144 | 36.2 | 87 | 63:68 |
| Della-2 | 162 | 42.3 | 91 | 62:68 |
| Mermentau | 186 | 39.8 | 88 | 64:71 |
| Wells | 203 | 44.1 | 88 | 63:71 |

In Table 25, agronomic characteristics are shown for rice cultivar RU1401105 and for four other rice cultivars. The data are the result of trials at the Cooperative Uniform Regional Rice Nursery (URRN) from 2014 for five locations, including Stuttgart, Ark.; Crowley, La.; Malden, Mo.; Stoneville, Miss.; and Beaumont, Tex. Column one shows the variety, columns two to six show the grain yield in bushels per acre for each of 5 different locations for each variety, column seven shows the average grain yield for the 5 locations, columns eight to twelve give the average head rice (%) to total rice (%) ratio for each of 5 different locations for each variety, and column thirteen shows the average head rice (%) to total rice (%) ratio for the 5 locations.

TABLE 25

| | GRAIN YIELD (BU/AC) | | | | | | HEAD RICE(%):TOTAL RICE(%) | | | | | |
|---|---|---|---|---|---|---|---|---|---|---|---|---|
| VARIETY | AR | LA | MO | MS | TX | AVG | AR | LA | MO | MS | TX | AVG |
| RU1401105 | 213 | 205 | 174 | 220 | 173 | 197 | 70:72 | 65:72 | 67:72 | 65:70 | 62:71 | 66:71 |
| Jazzman-2 | 175 | 180 | 197 | 191 | 153 | 179 | 69:72 | 72:72 | 68:72 | 64:70 | 64:72 | 68:72 |
| Della-2 | 175 | 248 | 229 | 189 | 173 | 203 | 68:71 | 66:72 | 63:71 | 62:68 | 65:72 | 65:71 |
| Mermentau | 221 | 234 | 210 | 185 | 191 | 208 | 70:73 | 70:73 | 68:74 | 55:69 | 61:71 | 65:72 |
| Wells | 251 | 209 | 204 | 193 | 208 | 213 | 69:74 | 62:72 | 64:74 | 50:69 | 64:73 | 62:72 |

In Table 26, agronomic characteristics are shown for rice cultivar RU1401105 and for five other rice cultivars. The data are the result of trials at the Cooperative Uniform Regional Rice Nursery (URRN) from 2015 for five locations, including Stuttgart, Ark.; Crowley, La.; Malden, Mo.; Stoneville, Miss.; and Beaumont, Tex. Column one shows the variety, columns two to six show the grain yield in bushels per acre for each of 5 different locations for each variety, column seven shows the average grain yield for the 5 locations, columns eight to twelve give the average head rice (%) to total rice (%) ratio for each of 5 different locations for each variety, and column thirteen shows the average head rice (%) to total rice (%) ratio for the 5 locations.

TABLE 26

| | GRAIN YIELD (BU/AC) | | | | | | HEAD RICE(%):TOTAL RICE(%) | | | | |
|---|---|---|---|---|---|---|---|---|---|---|---|
| VARIETY | AR | LA | MO | MS | TX | AVG | AR | LA | MS | TX | AVG |
| RU1401105 | 174 | 183 | 210 | 178 | 98 | 167 | 67:70 | 67:74 | 66:72 | 62:69 | 66:71 |
| RU1501102 | 152 | 162 | 181 | 167 | 144 | 161 | 64:69 | 60:73 | 61:71 | 55:68 | 60:70 |
| Jazzman-2 | 149 | 157 | 196 | 173 | 113 | 157 | 66:69 | 70:74 | 65:71 | 65:73 | 67:72 |
| Della-2 | 172 | 164 | 212 | 174 | 130 | 170 | 65:68 | 65:73 | 59:70 | 61:68 | 62:70 |
| Mermentau | 202 | 210 | 214 | 200 | 146 | 194 | 67:71 | 65:71 | 63:72 | 63:71 | 65:71 |
| Wells | 189 | 175 | 217 | 192 | 144 | 183 | 65:70 | 56:73 | 62:73 | 60:71 | 61:72 |

In Table 27, agronomic characteristics are shown for rice cultivar RU1401105 and for five other rice cultivars. The data are the result of trials at the Cooperative Uniform Regional Rice Nursery (URRN) from 2016 for five locations, including Stuttgart, Ark.; Crowley, La.; Malden, Mo.; Stoneville, Miss.; and Beaumont, Tex. Column one shows the variety, columns two to six show the grain yield in bushels per acre for each of 5 different locations for each variety, column seven shows the average grain yield for the 5 locations, columns eight to twelve give the average head rice (%) to total rice (%) ratio for each of 5 different locations for each variety, and column thirteen shows the average head rice (%) to total rice (%) ratio for the 5 locations.

TABLE 27

| | GRAIN YIELD (BU/AC) | | | | | | HEAD RICE(%):TOTAL RICE(%) | | | | | |
|---|---|---|---|---|---|---|---|---|---|---|---|---|
| VARIETY | AR | LA | MO | MS | TX | AVG | AR | LA | MO | MS | TX | AVG |
| RU1401105 | 139 | 180 | 162 | 187 | 113 | 156 | 61:69 | 68:73 | 65:73 | 66:70 | 63:70 | 64:71 |
| RU1501102 | 106 | 140 | 129 | 179 | 129 | 137 | 55:65 | 60:70 | 61:71 | 60:69 | 53:64 | 58:68 |
| Jazzman-2 | 115 | 155 | No Data | 165 | 102 | 135 | 55:63 | 65:72 | No Data | 67:71 | 61:70 | 62:69 |
| Della-2 | 137 | 185 | No Data | 175 | 120 | 154 | 57:64 | 64:70 | No Data | 65:69 | 58:68 | 61:68 |
| Mermentau | 125 | 200 | No Data | 199 | 165 | 172 | 56:67 | 63:71 | No Data | 66:71 | 61:71 | 61:70 |
| Wells | 162 | 192 | 175 | 211 | 176 | 183 | 60:70 | 62:72 | 60:74 | 61:71 | 48:70 | 58:71 |

In Table 28, agronomic characteristics are shown for rice cultivar RU1401105 and for five other rice cultivars. The data are the result of trials at the Cooperative Uniform Regional Rice Nursery (URRN) from 2017 for five locations, including Stuttgart, Ark.; Crowley, La.; Malden, Mo.; Stoneville, Miss.; and Beaumont, Tex. Column one shows the variety, columns two to six show the grain yield in bushels per acre for each of 5 different locations for each variety, column seven shows the average grain yield for the 5 locations, columns eight to twelve give the average head rice (%) to total rice (%) ratio for each of 5 different locations for each variety, and column thirteen shows the average head rice (%) to total rice (%) ratio for the 5 locations.

TABLE 28

| VARIETY | GRAIN YIELD (BU/AC) | | | | | | HEAD RICE(%):TOTAL RICE(%) | | | | | |
|---|---|---|---|---|---|---|---|---|---|---|---|---|
| | AR | LA | MO | MS | TX | AVG | AR | LA | MO | MS | TX | AVG |
| RU1401105 | 162 | 141 | | 220 | | 174 | 66:71 | 66:72 | | 68:73 | | 67:72 |
| RU151102 | 172 | 134 | | 219 | | 175 | 65:69 | 68:74 | | 69:73 | | 67:72 |
| Jazzman-2 | 137 | 118 | | 159 | | 138 | 62:67 | 67:73 | | 66:72 | | 65:71 |
| Delta-2 | 165 | 142 | | 175 | | 161 | 58:67 | 55:67 | | 62:71 | | 58:68 |
| Mermentau | 197 | 132 | | 217 | | 182 | 61:71 | 59:75 | | 66:71 | | 62:72 |
| Wells | 209 | 151 | | 237 | | 199 | 59:71 | 57:72 | | 62:73 | | 59:72 |

In Table 29, agronomic characteristics are shown for rice cultivar RU1401105 and for five other rice cultivars. The data are the mean from the Cooperative Uniform Regional Rice Nursery (URRN) trials conducted in 2014-2017 for five locations, including Stuttgart, Ark.; Crowley, La.; Malden, Mo.; Stoneville, Miss.; and Beaumont, Tex. Column one shows the variety, columns two to six show the grain yield in bushels per acre for each of 5 different locations for each variety, column seven shows the average grain yield for the 5 locations, columns eight to twelve give the average head rice (%) to total rice (%) ratio for each of 5 different locations for each variety, and column thirteen shows the average head rice (%) to total rice (%) ratio for the 5 locations.

TABLE 29

| VARIETY | GRAIN YIELD (BU/AC) | | | | | | HEAD RICE(%):TOTAL RICE(%) | | | | | |
|---|---|---|---|---|---|---|---|---|---|---|---|---|
| | AR | LA | MO | MS | TX | AVG | AR | LA | MO | MS | TX | AVG |
| RU1401105 | 172 | 177 | | 201 | | 183 | 66:71 | 67:73 | | 66:71 | | 66:72 |
| RU151102 | 143 | 145 | | 188 | | 159 | 61:68 | 63:72 | | 63:71 | | 62:70 |
| Jazzman-2 | 144 | 153 | | 172 | | 156 | 63:68 | 69:73 | | 66:71 | | 66:71 |
| Delta-2 | 162 | 185 | | 178 | | 175 | 62:68 | 63:71 | | 62:70 | | 62:70 |
| Mermentau | 186 | 194 | | 200 | | 193 | 64:71 | 64:73 | | 63:71 | | 64:72 |
| Wells | 203 | 182 | | 208 | | 198 | 63:71 | 59:72 | | 59:72 | | 60:72 |

In Table 30, kernel characteristics are shown for rice cultivar RU1401105 and for two other rice cultivars. The data are averages of the Arkansas Rice Performance Trials (ARPT) conducted in 2014-2016. Column one shows the variety, column two shows the mean kernel length in millimeters, column three shows the mean kernel width in millimeters, column four shows the mean kernel thickness in millimeters, column five shows the mean kernel length to width ratio, and column six shows the mean kernel weight in milligrams.

TABLE 30

| Variety | Length (mm) | Width (mm) | Thickness (mm) | L/W Ratio | Kernel Weight (mg) |
|---|---|---|---|---|---|
| RU1401105 | 7.31 | 2.16 | 1.75 | 3.39 | 21.7 |
| RU1501102 | 7.42 | 2.22 | 1.80 | 3.35 | 23.3 |
| Wells | 7.28 | 2.18 | 1.76 | 3.37 | 21.9 |

In Table 31, reactions to diseases are shown for rice cultivar RU1401105 and for seven other rice cultivars. Reactions were determined based on historical and recent observations from test plots and grower fields across Arkansas and other rice states in southern USA. In general, these ratings represent expected cultivar reactions to disease under conditions that most favor severe disease development. Plant reactions were rated using the standard disease ratings of R=Resistant: MR=Moderately Resistant; MS=Moderately Susceptible; S=Susceptible; VS=Very Susceptible in the Table below. Cells with no values indicate that there is no definitive Arkansas disease rating information available at this time.

TABLE 31

| Cultivar | Sheath Blight | Blast | Straighthead | Bacterial Panicle Blight | Narrow Brown Leaf Spot | Stem Rot | Kernel Smut | False Smut |
|---|---|---|---|---|---|---|---|---|
| RU1401105 | MS | MS | — | MR | — | — | — | S |
| RU1501102 | MS | MS | — | MR | — | — | — | MR |
| Della-2 | S | R | — | MS | S | — | — | — |
| Jazzman-2 | S | MS | — | VS | S | — | S | S |
| LaKast | MS | S | MS | MS | MS | S | S | S |
| Roy J | MS | S | S | S | R | S | VS | S |
| Taggart | MS | MS | R | MS | MS | S | S | S |
| Wells | S | S | S | S | S | VS | S | S |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Deposit Information

A deposit of the Board of Trustees of the University Of Arkansas proprietary rice cultivar RU1401105 disclosed above and recited in the appended claims has been made with the American Type Culture Collection (ATCC), 10801 University Boulevard, Manassas, Va. 20110. The date of deposit was Jun. 25, 2019. The deposit of 2,500 seeds was taken from the same deposit maintained by the Board of Trustees of the University Of Arkansas since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126031. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A rice seed of the variety 'RU1401105,' a representative sample of seed of said variety having been deposited under ATCC Accession No. PTA-126031.

2. A rice plant, or a part thereof, produced by growing the seed of claim 1.

3. A method for producing rice plants, said method comprising planting a plurality of rice seeds as recited in claim 1 under conditions favorable for the growth of rice plants.

4. The method of claim 3, additionally comprising the step of producing rice seed from the resulting rice plants.

5. A rice seed produced by the method of claim 4.

6. Pollen or an ovule of the plant of claim 2.

7. A rice plant, or a part thereof having all of the physiological and morphological characteristics of the rice plant of claim 2.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all of the morphological and physiological characteristics of 'RU1401105'.

11. A method for producing rice seed, said method comprising crossing a first parent rice plant with a second parent rice plant, and harvesting the resulting $F_1$ hybrid rice seed, wherein the first parent rice plant or the second parent rice plant is the rice plant of claim 2.

12. A rice seed produced by the method of claim 11.

13. The rice seed of claim 12, wherein the rice plants grown from said rice seed will express the characteristics of 'RU1401105.'

14. The method of claim 11, wherein one of said rice plants is transgenic and the other is a rice plant of cultivar 'RU1401105'.

15. The method of claim 11, additionally comprising the step of planting a plurality of the rice seed under conditions favorable for the growth of rice plants.

16. The method of claim 15, additionally comprising the step of producing rice seed from the resulting rice plants; wherein, if the resulting rice seed is grown, then at least some rice plants grown from the resulting rice seed will express the characteristics of 'RU1401105.'

17. A method comprising transforming the rice plant of claim 2 with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

18. A rice plant or part thereof, or rice seed, produced by the method of claim 17.

19. An herbicide resistant rice plant produced by the method of claim 17, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

20. A method of introducing a desired trait into rice cultivar 'RU1401105,' said method comprising the steps of:
    (a) crossing plants as recited in claim 2 with plants of another rice line expressing the desired trait, to produce progeny plants;
    (b) selecting progeny plants that express the desired trait, to produce selected progeny plants;
    (c) crossing the selected progeny plants with plants from the 'RU1401105' parental line to produce new progeny plants;
    (d) selecting new progeny plants that express both the desired trait and some or all of the physiological and morphological characteristics of rice cultivar 'RU1401105,' to produce new selected progeny plants; and
    (e) repeating steps (c) and (d) three or more times in succession, to produce selected higher generation backcross progeny plants that express both the desired trait and all of the physiological and morphological characteristics of rice cultivar 'RU1401105,' when grown in the same environmental conditions.

21. The method of claim 20, additionally comprising the step of planting a plurality of rice seed produced by selected higher generation backcross progeny plants under conditions favorable for the growth of rice plants and optionally comprising the step of producing rice seed from the resulting rice plants.

22. The rice seed resulting from the method of claim 21, wherein, if the resulting rice seed is grown, then the rice plants grown from the resulting rice seed express the desired trait.

* * * * *